US009523069B2

(12) United States Patent
Jeong et al.

(10) Patent No.: US 9,523,069 B2
(45) Date of Patent: Dec. 20, 2016

(54) PHOTOBIOREACTOR FOR MICROALGAE CULTIVATION HAVING ARC-TYPE PARTITION STRUCTURE FOR FORMING VORTICES

(71) Applicant: INDUSTRY-ACADEMIC COOPERATION FOUNDATION, CHOSUN UNIVERSITY, Gwangju (KR)

(72) Inventors: Sang Hwa Jeong, Gwangju (KR); Jong Rak Park, Gwangju (KR); Jong Tye Kim, Gwangju (KR); Dong Gyu Ahn, Gwangju (KR); Jeong Woo Park, Gwangju (KR)

(73) Assignee: INDUSTRY-ACADEMIC COOPERATION FOUNDATION, CHOSUN UNIVERSITY, Gwangju (KR)

( * ) Notice: Subject to any disclaimer, the term of this patent is extended or adjusted under 35 U.S.C. 154(b) by 120 days.

(21) Appl. No.: 14/574,773

(22) Filed: Dec. 18, 2014

(65) Prior Publication Data
US 2015/0175946 A1    Jun. 25, 2015

Related U.S. Application Data

(63) Continuation of application No. PCT/KR2012/006442, filed on Aug. 13, 2012.

(30) Foreign Application Priority Data

Jun. 19, 2012 (KR) .................. 10-2012-0065687

(51) Int. Cl.
C12M 1/04     (2006.01)
C12M 1/00     (2006.01)
(Continued)

(52) U.S. Cl.
CPC ............. *C12M 21/02* (2013.01); *C12M 23/04* (2013.01); *C12M 27/20* (2013.01); *C12M 29/06* (2013.01); *C12N 1/12* (2013.01)

(58) Field of Classification Search
CPC ....... C12M 27/20; C12M 23/04; C12M 29/06; C12N 1/12
(Continued)

(56) References Cited

U.S. PATENT DOCUMENTS 6,509,188 B1    1/2003  Trosch et al.
8,650,798 B1 *  2/2014  Armstrong ............... C12N 1/12
                                                  47/1.4

(Continued)

FOREIGN PATENT DOCUMENTS

JP    2010511411 A    4/2010
KR    20020008825 A   1/2002
(Continued)

OTHER PUBLICATIONS

PCT International Search Report dated Feb. 27, 2013 for PCT/KR2012/006442, from which the instant application is based, 4 pgs.

*Primary Examiner* — William H Beisner
(74) *Attorney, Agent, or Firm* — Fredrikson & Byron, P.A.

(57) ABSTRACT

The present invention relates to a photobioreactor for microalgae cultivation having a bubble circulation structure, which allows gas flowing into a cultivation space to generate a vortex and thus circulate microalgae, thereby improving cultivation efficiency of the microalgae.

A photobioreactor for microalgae cultivation according to an embodiment of the present invention includes a cultivation panel major body having the cultivation space into which the microalgae are injected to be cultivated; a gas supply pipe provided at a lower portion of the cultivation panel major body to pass through the cultivation space in a transverse
(Continued)

direction and thus discharge inflow gas; and at least one vortex forming partition extending in a transverse direction from an internal wall of the cultivation panel major body and formed to have an arc shape and thus cause a vortex to an ascending current of gas supplied through the gas supply pipe.

6 Claims, 5 Drawing Sheets

(51) Int. Cl.
     *C12M 1/12*      (2006.01)
     *C12N 1/12*      (2006.01)

(58) Field of Classification Search
     USPC .................................................. 435/292.1
     See application file for complete search history.

(56) References Cited

U.S. PATENT DOCUMENTS

| | | | | |
|---|---|---|---|---|
| 2003/0059932 | A1* | 3/2003 | Craigie | C12M 21/02 |
| | | | | 435/292.1 |
| 2005/0064577 | A1* | 3/2005 | Berzin | B01D 53/85 |
| | | | | 435/266 |
| 2008/0274494 | A1* | 11/2008 | Kertz | A01G 7/02 |
| | | | | 435/29 |
| 2010/0178693 | A1 | 7/2010 | Furukawa et al. | |
| 2010/0323436 | A1 | 12/2010 | Lee et al. | |

FOREIGN PATENT DOCUMENTS

| | | |
|---|---|---|
| KR | 1020090055169 A | 6/2009 |
| KR | 1020110094830 A | 8/2011 |

\* cited by examiner

FIG5
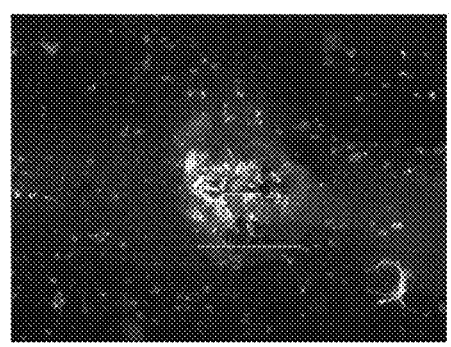
(a)
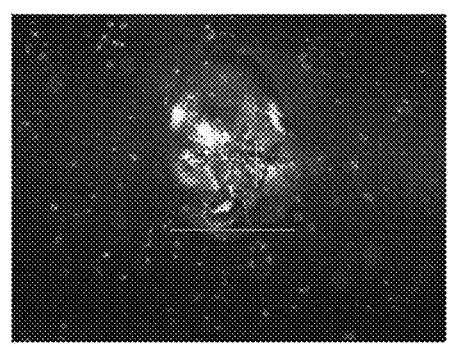
(b)
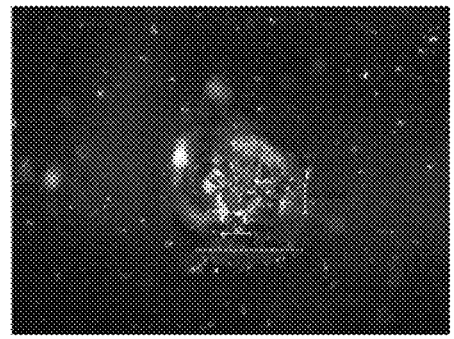
(c)

PHOTOBIOREACTOR FOR MICROALGAE CULTIVATION HAVING ARC-TYPE PARTITION STRUCTURE FOR FORMING VORTICES

RELATED APPLICATIONS

This is a continuation of International Application No. PCT/KR2012/006442 filed Aug. 13, 2012, which claims priority to Korean Application No. 10-2012-0065687 filed Jun. 19, 2012, the contents of both of which are incorporated by reference herein.

TECHNICAL FIELD

The present disclosure relates to a photobioreactor for cultivating microalgae, and more particularly, to a photobioreactor for microalgae cultivation having an arc type partition structure for forming a vortex, which allows gas flowing into a cultivation space to generate the vortex in a predetermined direction and thus circulate microalgae, thereby improving cultivation efficiency of the microalgae.

BACKGROUND ART

Recently, carbon dioxide ($CO_2$) discharged from industrial factories have been pointed out as a main culprit of global warming, accordingly, research to fix carbon dioxide and use microalgae as a bioenergy source has been actively conducted. The microalgae can function to treat waste water and fix carbon dioxide because of various abilities thereof, and have been used for the purpose of producing useful materials such as fuel materials, cosmetics, feed, food coloring, and medical raw materials, and a utilization range of the microalgae has expanded due to the continuous discovery of useful high-value materials.

Many factors such as composition of a culture medium, temperature, acidity (pH), intensity of light, and amount of light are present as a matter affecting an increase in weight of living bodies and useful products of the microalgae, but among the factors, the proportion of light is largest due to a property of photosynthetic microalgae.

Generally, apparatuses for cultivating the photosynthetic microalgae for the purpose of securing a biomass and fixing carbon dioxide may be largely divided into an apparatus of performing large-scale outdoor cultivation (open system) and an apparatus of using a photobioreactor (closed system). In the case of the apparatus of performing large-scale outdoor cultivation, which includes a pond type, reaction facilities such as a lake or large-scale pond type have been mainly used, and commercialized in some countries.

However, the aforementioned type of cultivation facilities have merits in that an initial investment cost is low and maintenance is easy, but installation thereof has no choice but to be extremely restrictive because of problems such as contamination, difficulty in separation and purification, a low cell concentration, a large substrate amount (particularly, nitrogen source), requirement of high water quality and large water amount, an irregular climate condition, and high personnel expenses. Particularly, there are demerits in that since light is not effectively transmitted into the cultivation apparatus, a growth rate of a fungus body is slow, growth yield of the fungus body is low, and a wide installation space is required in order to remove a large amount of carbon dioxide.

In order to solve the aforementioned problems of the apparatus of performing large-scale outdoor cultivation, efforts for producing products in an amount that is the same as or larger than the amount in the apparatus of performing large-scale outdoor cultivation and producing high-quality products including useful materials at a higher concentration by performing high concentration cultivation through a small-scale reactor are being made.

As a currently developed type, there are a general agitation-type reactor, a plate-type reactor, a pipe-type reactor, a column-type reactor, and the like, and in all kinds of the reactors, effective transmission of light is considered as a most important point in design of the reactor. When the concentration of the microalgae cell is low, a culture medium, injection of gas, and the like are the most important factors, but when the concentration reaches a high concentration, the intensity of light becomes the most important factor. This is because as the concentration is increased, a penetration length of light is shortened.

That is, in the case of light applied while the microalgae are cultivated, a population number is gradually increased while the microalgae grow, and thus the microalgae existing on the surface of the reactor can continuously receive light, but the microalgae in the reactor cannot receive a sufficient amount of light required in growth because a shadow effect is formed due to the microalgae of the surface.

In order to solve this problem, Korean Patent No. 10-0933741 discloses a photobioreactor for cultivating microalgae in a large amount. In the disclosed reactor, a LED and a flexible LED are used as a plate-type light source, and the reactor has a structure where the light source comes into direct contact with a cultivation solution.

However, in the photobioreactor having the aforementioned structure, there is a problem in that, since microalgae are attached to the surface of the light source, light efficiency is reduced.

Further, as a technology relating to the photobioreactor, Korean Patent Application Laid-Open No. 2002-0008825 discloses a photobioreactor of producing biological resources, which includes an apparatus causing turbulence fluidization, a device introducing light into a reactor chamber, and an apparatus injecting air at a lower side of the reactor chamber. However, the aforementioned photobioreactor adopts a structure where algae and air are mixed by injecting air at the lower side, but has a problem in that when an injection pressure of air is reduced, the algae may be added into the apparatus injecting air.

DISCLOSURE OF THE INVENTION

Technical Problem

One object of the present invention is to provide a photobioreactor of allowing microalgae in a cultivation space to uniformly receive carbon dioxide gas and sun light and thus improve cultivation efficiency by generating a vortex in the microalgae injected into the cultivation space to perform circulation.

Another object of the present invention is to provide a photobioreactor of generating a vortex of microalgae in a predetermined direction to more effectively circulate the microalgae.

Still another object of the present invention is to provide a photobioreactor in which an outlet provided in a flexible gas supply pipe made of an elastic material is opened by expansion at a predetermined pressure or more to prevent flowing of microalgae into the gas supply pipe.

However, the object of the present invention is not limited to the aforementioned objects, and unmentioned other objects may be clearly understood by the person with ordinary skill in the art from the following description.

Technical Solution

In order to achieve the objects, the present invention provides a photobioreactor for microalgae cultivation, including a cultivation panel major body having a cultivation space into which microalgae are injected to be cultivated and support ribs formed at regular intervals on an external surface thereof; a gas supply pipe provided at a lower portion of the cultivation panel major body to pass through the cultivation space in a transverse direction and thus discharge inflow gas; and at least one vortex forming partition extending in a transverse direction from an internal wall of the cultivation panel major body and formed to have an arc shape and thus cause a vortex to an ascending current of the gas supplied through the gas supply pipe, in which the support ribs are provided to prevent distortion of the cultivation panel major body through the ascending current of the gas.

The gas supply pipe has a plurality of outlets having surfaces expanding at a predetermined pressure or more to supply the gas in a bubble curtain mode through the plurality of outlets so that a constant pressure is maintained in the cultivation panel major body and thus provide bubbles uniformly present over an entire region to an incubator.

The photobioreactor according to the present invention includes a main body formed to have a quadrangular frame shape and including a plurality of fastening units formed at regular intervals on an external surface thereof; and front and rear surface covers formed of a transparent material and combined at front and rear surfaces of the main body to form the cultivation space, and the fastening units fix the support ribs through fastening units formed on a same line in a horizontal direction.

In the photobioreactor according to the present invention, the vortex forming partition includes a first vortex forming partition extending in a transverse direction from an internal wall of the main body at a position upwardly spaced apart from the gas supply pipe, formed to have an arc shape so that a spacing distance between a first lower end formed at a position coming into close contact with the rear surface cover and the gas supply pipe is shorter than a spacing distance between a first upper end facing the front surface cover and the gas supply pipe, and formed so that a first spacing distance is maintained between the first vortex forming partition and an upper surface of the main body; and a second vortex forming partition extending in a transverse direction from an internal wall of the main body at a position upwardly spaced apart from the first vortex forming partition, formed to have an arc shape so that a spacing distance between a second upper end formed at a position coming into close contact with the front surface cover and the gas supply pipe is shorter than a spacing distance between a second lower end facing the lower cover and the gas supply pipe, and formed so that a second spacing distance is maintained between the second vortex forming partition and a lower surface of the main body.

In the photobioreactor according to the present invention, at least one independent vortex generation blade is attached to internal sides of the first vortex forming partition and the second vortex forming partition to cause a vortex in a predetermined direction.

The photobioreactor according to the present invention further includes a microalgae injection pipe provided at a side of a lower end of the cultivation panel major body to inject the microalgae into the cultivation space; a microalgae emission pipe provided at an upper end of a lateral surface of the cultivation panel major body to emit the microalgae cultivated in the cultivation space to an outside; and a gas discharge hole provided at an upper end of the cultivation panel major body to discharge the gas ascending from the cultivation space to the outside.

Advantageous Effects

According to a photobioreactor of the present invention, there is a merit in that a vortex can be formed by a partition for vortex formation while gas supplied through a gas supply pipe having a plurality of outlets ascends to increase a gas retention time in a cultivation space and cause a flow of microalgae, thus uniformalizing a light absorption condition of the microalgae.

Further, according to the photobioreactor of the present invention, there is a merit in that a photobioreactor in which the outlets provided in the flexible gas supply pipe made of an elastic material can be opened by expansion at a predetermined pressure or more to prevent flowing of the microalgae into the gas supply pipe.

Further, there is a merit in that even though a length of the supply pipe is increased, bubbles can be uniformly formed over an entire region.

BRIEF DESCRIPTION OF THE DRAWINGS

FIG. 5A is an illustrative view showing an outlet formed in a gas supply pipe of the photobioreactor according to the present invention.

FIG. 5B is an illustrative view showing an outlet formed in a gas supply pipe of the photobioreactor according to the present invention.

FIG. 5C is an illustrative view showing an outlet formed in a gas supply pipe of the photobioreactor according to the present invention.

MODE FOR CARRYING OUT THE INVENTION

Figure 1:
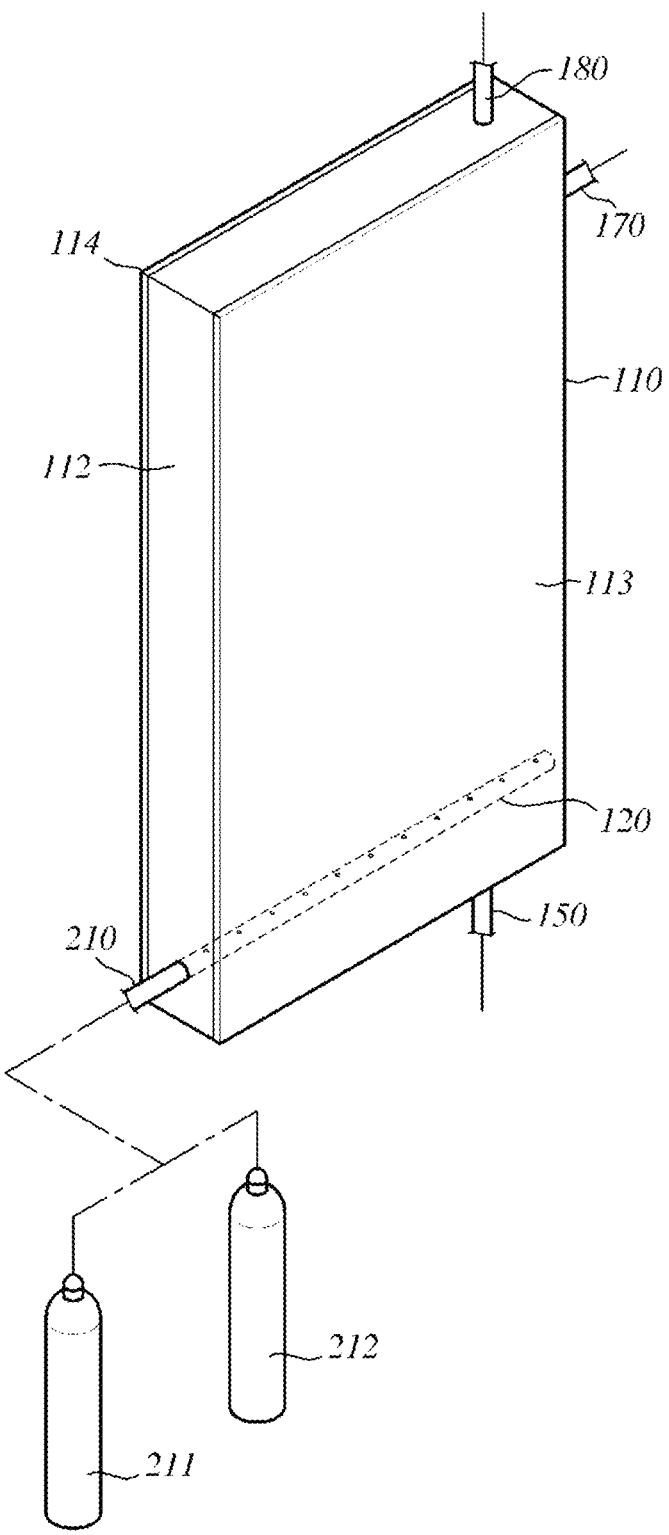
FIG. 1 is a perspective view showing a photobioreactor according to the present invention.

Hereinafter, detailed descriptions of preferred embodiments of the present invention will be given with reference to the accompanying drawings. In the description of the present invention, the detailed descriptions of known relating functions or constitutions thereof may be omitted if they make the gist of the present invention unclear.

The embodiments according to the concept of the present invention may be variously modified and have various forms, accordingly, predetermined embodiments will be shown in the drawings and described in detail in the present specification or application. However, it should be understood that the embodiments according to the concept of the present invention are not to be construed to be limited to specific disclosure forms but are set forth to include all modifications, equivalents, or substitutes thereof included in the spirit and scope of the present invention.

It will be understood that when a constitutional element is referred to as being "connected to" or "coupled to" another constitutional element, it can be directly connected or coupled to the other constitutional element or intervening constitutional elements may be present. In contrast, it will be understood that when a constitutional element is referred to as being "directly connected to" or "directly coupled to" another constitutional element, there are no intervening constitutional elements present. Other expressions describing the relationship between the constitutional elements, that is, "between" and "directly between" or "adjacent to" and "directly adjacent to", must be interpreted likewise.

The terminology used herein is for the purpose of describing particular embodiments only and is not intended to be limiting of the invention. The singular forms are intended to include the plural forms as well, unless the context clearly indicates otherwise. It will be further understood that the terms "comprises" or "has" when used in this specification, specify the presence of stated features, integers, steps, operations, constitutional elements, components, or combinations thereof, but do not preclude the presence or addition of one or more other features, integers, steps, operations, constitutional elements, components, or combinations thereof.

Figure 2:
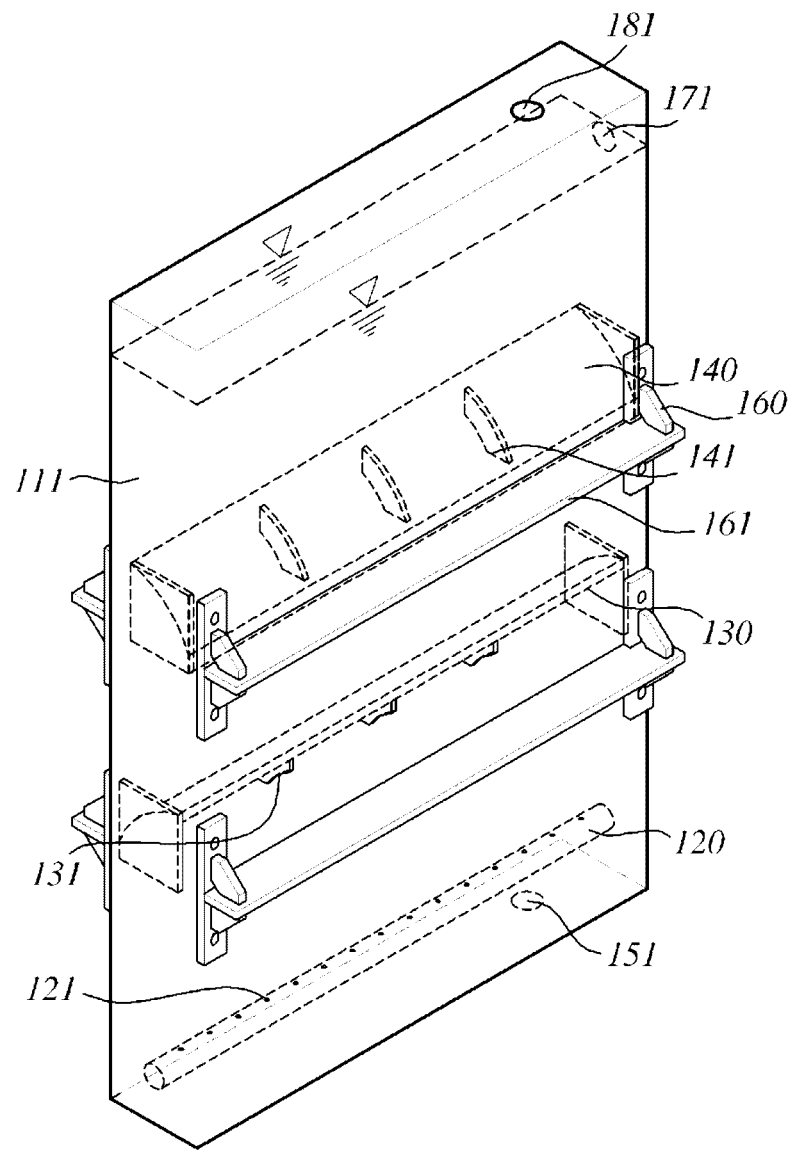
FIG. 2 is a perspective view showing a cultivation panel major body in the photobioreactor according to the present invention.
Figure 3:
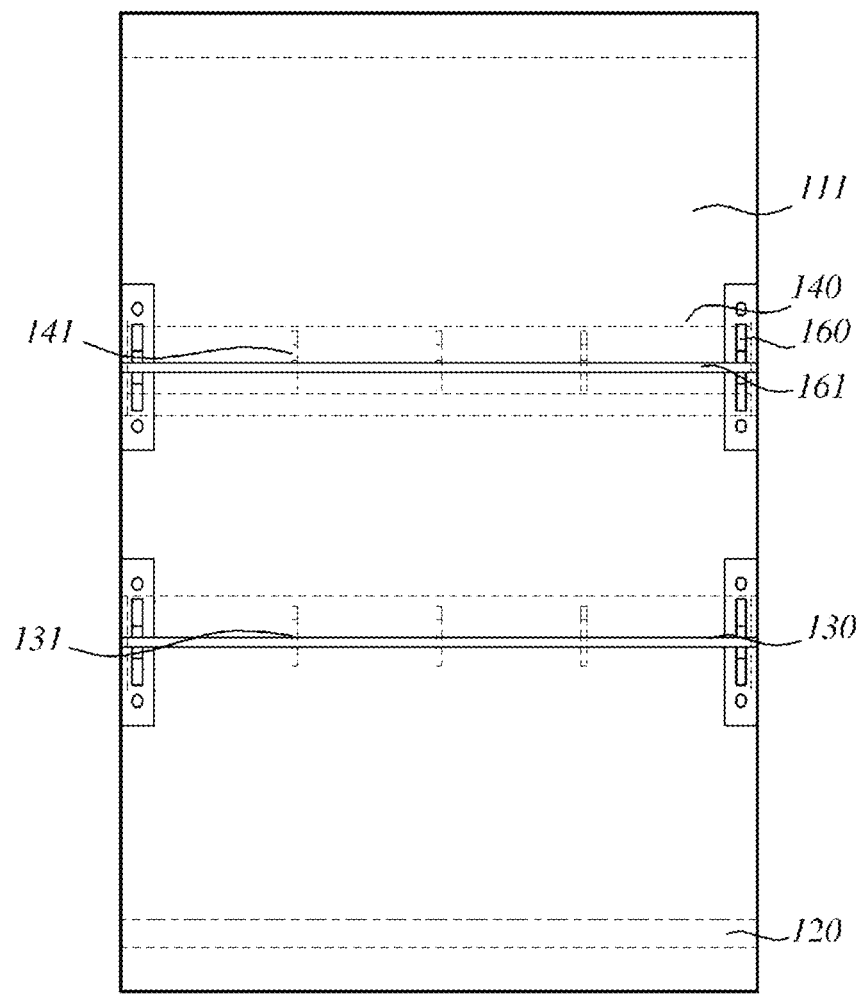
FIG. 3 is a front view of the cultivation panel major body of FIG. 2.
Figure 4:
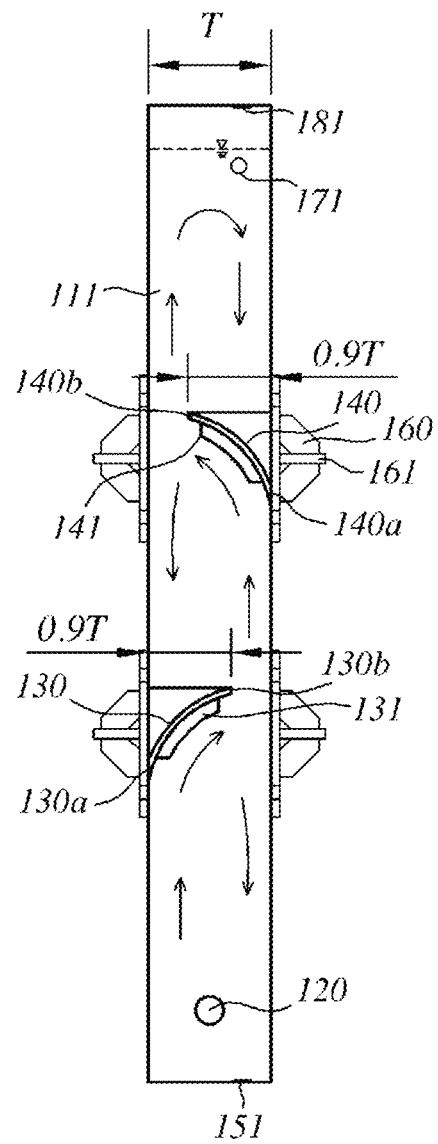
FIG. 4 is a side view of the cultivation panel major body of FIG. 2.

FIG. 1 is a perspective view showing a photobioreactor according to the present invention, FIG. 2 is a perspective view showing a cultivation panel major body in the photobioreactor according to the present invention, FIG. 3 is a front view of the cultivation panel major body of FIG. 2, and FIG. 4 is a side view of the cultivation panel major body of FIG. 2.

Referring to FIGS. 1 to 4, a photobioreactor 100 according to the present invention includes a cultivation panel major body 110, a gas supply pipe 120, a first vortex forming partition 130, and a second vortex forming partition 140.

The cultivation panel major body 110 is formed to have a quadrangular shape and include a cultivation space 111 into which microalgae are injected to be cultivated. The cultivation panel major body 110 may include a main body 112 formed to have a rectangular frame shape, and a front surface cover 113 and a rear surface cover 114 made of a transparent material to be combined at front and rear surfaces of the main body 112 and thus form the closed cultivation space 111.

Further, fastening units 160 are provided on the same line in a horizontal direction at regular intervals on external surfaces of the main body 112 to form pairs, and support ribs 161 are fastened between the fastening units 160.

The support ribs 161 are provided to prevent distortion of the main body 112 through a gas vortex generated in the main body 112.

Further, the fastening units 160 are formed to fix the support ribs 161 in a fastening mode, and in the present invention, the shape of the fastening unit is limited to a trapezoid having a fastening groove formed at the center thereof, but any shape can be used as long as the shape can fix the support ribs.

Further, an emission pipe 170 is combined with an upper side of a lateral surface of the main body 112 through an emission hole 171 formed through the main body 112 to emit the microalgae cultivated in the cultivation space 111 to the outside.

Further, the gas supply pipe 120 is provided at a lower end portion of the main body 112 to pass through the cultivation space 111 in a transverse direction and thus discharge inflow gas.

An injection pipe 150 is provided at the lower end of the main body 112 through an injection hole 151 formed to inject the microalgae into the cultivation space 111.

Although not shown in the drawings, the front surface cover 113 and the rear surface cover 114 may be combined with the main body 112 by a bolt and a nut, and may be combined with the main body by any various methods as long as the method can have a constitution where the front surface cover 113 and the rear surface cover 114 are attached to the main body 112 to prevent leakage of the microalgae injected into the cultivation space 111 to the outside.

Although not shown in the drawings, sensors, such as a turbidity measurement sensor which can measure turbidity of the cultivation space 111 or an acidity measurement sensor which can measure acidity (pH) of the cultivation space, may be further provided in the main body 112 of the cultivation panel major body 110 if necessary.

Further, a gas discharge hole 181 may be formed in a side of an upper portion of the main body 112 to discharge gas ascending from the cultivation space 111 to the outside, and a gas discharge pipe 180 may be connected thereto. A valve may be further included in the gas discharge pipe 180 to open and close the gas discharge pipe 180.

Meanwhile, the gas supply pipe 120 has a plurality of outlets 121 having surfaces expanding at a predetermined pressure or more, and gas is supplied in a bubble curtain mode through a plurality of outlets 121 to maintain a predetermined pressure in the cultivation panel major body 110, and thus the gas supply pipe functions to supply bubbles uniformly present over an entire region to an incubator.

Preferably, as shown in FIGS. 5A to 5C, the outlets 121 may be formed to have a diameter of approximately 180 μm, 103 μm, and 133 μm. Further, a plurality of outlets 121 formed in the gas supply pipe 120 are formed at regular intervals to uniformly supply the bubbles over an entire internal space in a fine bubble curtain mode.

Further, gas discharged through each outlet 121 forms bubbles in the microalgae, and it is preferable that the formed bubbles have a diameter of 0.5 to 2.0 mm. Further, it is preferable that an amount of the supplied bubbles be 5 to 10 cc/min per L, and the bubbles be supplied at a pressure of 1 to 3 $kg_f/cm^2$.

The first vortex forming partition 130 and the second vortex forming partition 140 each extend in a transverse direction from an internal wall of the main body 112 of the cultivation panel major body 110 and are formed to have an arc shape and thus form a vortex in the microalgae by an ascending current of gas supplied through the gas supply pipe 120.

The first vortex forming partition 130 extends in a transverse direction from the internal wall of the main body 112 at a position upwardly spaced apart from the gas supply pipe 120, is formed to have the arc shape so that a spacing distance between a first lower end 130a formed at a position coming into close contact with the rear surface cover 114 and the gas supply pipe 120 is shorter than a spacing distance between a first upper end 130b facing the front surface cover 113 and the gas supply pipe 120, and is formed so that a first spacing distance is maintained between the first vortex forming partition and a front surface of the main body 112.

Preferably, a fluidization path of the microalgae and gas may be provided through a space of the first spacing distance between the front surface of the main body 112 and the first upper end 130b of the first vortex forming partition 130 by setting a width of the main body 112 to T and setting a width of a horizontal distance of the first lower end 130a and the first upper end 130b to 0.9 T.

The second vortex forming partition 140 is formed to extend in a transverse direction from the internal wall of the main body 112 at a position upwardly spaced apart from the first vortex forming partition 130. The second vortex forming partition 140 is formed to have the arc shape so that a spacing distance between a second lower end 140a formed at a position coming into close contact with the front surface cover 113 and the gas supply pipe 120 is shorter than a spacing distance between a second upper end 140b facing the rear surface cover 114 and the gas supply pipe 120, and is formed so that a second spacing distance is maintained between the second lower end 140a and the rear surface of the main body 112.

Preferably, the fluidization path of the microalgae and gas may be provided through a space of the second spacing distance between the rear surface of the main body 112 and the second upper end 140b of the second vortex forming partition 140 by setting the width of the main body 112 to T and setting a width of a horizontal distance of the second lower end 140a and the second upper end 140b to 0.9 T.

Further, a plurality of independent vortex generation blades 131 and 141 are attached to internal sides of the first vortex forming partition 130 and the second vortex forming partition 140.

Accordingly, when the vortex of the microalgae is generated by the first vortex forming partition 130 and the second vortex forming partition 140, the vortex can be generated in a predetermined direction.

Meanwhile, it is preferable that titanium dioxide (TiO) be applied on the internal wall of the cultivation panel major body 110 to form a coating film and thus prevent attachment of the microalgae to the internal wall. Further, a filter blocking ultraviolet and infrared rays may be formed on the external or internal surface of the cultivation panel major body 110 to allow the microalgae to grow.

A gas supply unit 210 is configured to supply gas through the gas supply pipe 120. The gas supply unit 210 supplies mixture gas through a first tank 211 containing carbon dioxide and a second tank 212 containing air such as oxygen to the gas supply pipe 120.

Although not shown in the drawings, a gas tank for supplying gas other than carbon dioxide and oxygen may be further provided in the gas supply unit 210 according to a type of microalgae cultivated in the cultivation panel major body 112.

After the microalgae as a cultivation target is injected through the injection pipe 150 into the photobioreactor 100, supply target gas is supplied from the gas supply unit 210 through the gas supply pipe 120 to cultivate the microalgae.

For an amount of the microalgae injected into the cultivation space 111, the microalgae may be injected at a position that is lower than that of the gas discharge hole 181 and higher than that of the emission hole 171.

During a cultivation process, gas supplied through the gas supply pipe 120 ascends in the cultivation space 111 to form a current downwardly rotating due to interference of the first vortex forming partition 130, a retention position of the microalgae in the cultivation space 111 is not limited due to the vortex but the microalgae is circulated, and the current discharged from a gap between the first upper end 130b of the first vortex forming partition 130 and the front surface cover 113 forms the vortex again due to the second vortex forming partition 140 as described above. In addition, gas ascending to the uppermost portion of the cultivation space 111 is discharged through the gas discharge hole 181 to the outside.

A retention time of gas in the cultivation space 111 may be increased and an action position of the microalgae may become random due to the aforementioned vortex forming structure to reduce an absorption deviation of radiated light and thus allow the microalgae to uniformly grow.

Meanwhile, although not shown in the drawings, in addition to sun light, an auxiliary light source unit having a lamp may be further provided in the photobioreactor 100 to be adjacent to the cultivation panel major body 110 and thus radiate light on the cultivation panel major body 110.

The present invention has been described with reference to the exemplary embodiments shown in the drawings in an illustrative manner, and a person with ordinary skill in the art will understand that many modifications and other equivalent exemplary embodiments of the present invention are possible in light of the above teachings. Accordingly, the actual technical scope of the present invention must be determined by the spirit of the appended claims.

| [Explanation of Reference Numerals and Symbols] | |
|---|---|
| 100: photobioincubator | 110: cultivation panel major body |
| 120: gas supply pipe | 130: first vortex forming partition |
| 131: first independent vortex generation blade | 140: second vortex forming partition |
| 141: second independent vortex generation blade | 150: injection pipe |
| 180: gas discharge pipe | 160: fastening unit |
| 161: support rib | 170: emission pipe |
| 210: gas supply unit | |

The invention claimed is:

1. A photobioreactor for microalgae cultivation, comprising:
a cultivation panel major body having a cultivation space into which microalgae are injected to be cultivated and support ribs formed at regular intervals on an external surface thereof;
a gas supply pipe provided at a lower portion of the cultivation panel major body to pass through the cultivation space in a transverse direction and thus discharge inflow gas; and
at least one vortex forming partition extending in a transverse direction from an internal wall of the cultivation panel major body and formed to have an arc shape and thus cause a vortex to an ascending current of the gas supplied through the gas supply pipe, the support ribs being formed at intervals corresponding to the location of the at least one vortex forming partition, such that the support ribs
prevent deformation of shapes of a front surface cover and a rear surface cover due to a water pressure generated according to filling of a cultivation solution or the microalgae in the cultivation panel major body and distortion of the cultivation panel major body through the ascending current of the gas.

2. The photobioreactor as set forth in claim 1, wherein the gas supply pipe has a plurality of outlets having surfaces expanding at a predetermined pressure or more to supply the gas in a bubble curtain mode through the plurality of outlets so that a constant pressure is maintained in the cultivation panel major body and thus provide bubbles uniformly present over an entire region to an incubator.

3. The photobioreactor as set forth in claim 1, wherein the cultivation panel major body includes a main body formed internally therewithin to have a quadrangular frame shape and including a plurality of fastening units formed at regular intervals on an external surface thereof; and front and rear surface covers formed of a transparent material and combined at front and rear surfaces of the main body to form the cultivation space each support rib being fixed to the front and rear surfaces of the main body along a horizontal line, the fastening units being configured to fix the support ribs on opposite ends of the horizontal line.

4. The photobioreactor as set forth in claim 3, wherein the vortex forming partition includes
   a first vortex forming partition extending in a transverse direction from an internal wall of the main body at a position upwardly spaced apart from the gas supply pipe, formed to have an arc shape so that a spacing distance between a first lower end formed at a position coming into close contact with the rear surface cover and the gas supply pipe is shorter than a spacing distance between a first upper end facing the front surface cover and the gas supply pipe, and formed so that a first spacing distance is maintained between the first vortex forming partition and the front surface of the main body; and
   a second vortex forming partition extending in a transverse direction from an internal wall of the main body at a position upwardly spaced apart from the first vortex forming partition, formed to have an arc shape so that a spacing distance between a second lower end formed at a position coming into close contact with the front surface cover and the gas supply pipe is shorter than a spacing distance between a second upper end facing the lower cover and the gas supply pipe, and formed so that a second spacing distance is maintained between the second vortex forming partition and the rear surface of the main body.

5. The photobioreactor as set forth in claim 4, wherein at least one independent vortex generation blade is attached to internal sides of the first vortex forming partition and the second vortex forming partition to cause a vortex in a predetermined direction.

6. The photobioreactor as set forth in claim 1, further comprising:
   a microalgae injection pipe provided at a side of a lower end of the cultivation panel major body to inject the microalgae into the cultivation space;
   a microalgae emission pipe provided at an upper end of a lateral surface the cultivation panel major body to emit the microalgae cultivated in the cultivation space to an outside; and
   a gas discharge hole provided at an upper end of the cultivation panel major body to discharge the gas ascending from the cultivation space to the outside.

* * * * *